United States Patent
Bhattacharya

(10) Patent No.: US 10,245,002 B2
(45) Date of Patent: Apr. 2, 2019

(54) ISOTOPE SPECIFIC CALIBRATION OF A DOSE CALIBRATOR FOR QUANTITATIVE FUNCTIONAL IMAGING

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/666,424

(22) Filed: Aug. 1, 2017

(65) Prior Publication Data

US 2019/0038252 A1  Feb. 7, 2019

(51) Int. Cl.
*A61B 6/00* (2006.01)
*A61B 6/03* (2006.01)

(52) U.S. Cl.
CPC .............. *A61B 6/582* (2013.01); *A61B 6/037* (2013.01)

(58) Field of Classification Search
CPC ................................ A61B 6/037; A61B 6/582
USPC ...... 250/252.1, 363.04, 362, 363.03, 363.02, 250/363.1
See application file for complete search history.

(56) References Cited

U.S. PATENT DOCUMENTS

| | | | | |
|---|---|---|---|---|
| 3,271,315 A * | 9/1966 | McCabe | ............... | C07C 51/09 508/485 |
| 4,122,339 A * | 10/1978 | Smith, Jr. | ............. | G01V 5/105 250/264 |
| 4,568,828 A * | 2/1986 | Collica | ................ | G01T 1/02 250/252.1 |
| 4,880,981 A * | 11/1989 | Johnston | ............... | G01T 1/203 250/361 R |
| 2005/0152835 A1* | 7/2005 | Pak | ................... | A61K 51/0402 424/1.11 |
| 2005/0225751 A1* | 10/2005 | Sandell | ............... | B01L 3/5025 356/236 |
| 2007/0040115 A1* | 2/2007 | Publicover | ............. | G01T 1/29 250/305 |
| 2008/0033291 A1* | 2/2008 | Rousso | .............. | A61B 5/02755 600/436 |
| 2008/0042067 A1* | 2/2008 | Rousso | ................ | A61B 5/417 250/363.04 |
| 2008/0128626 A1* | 6/2008 | Rousso | ................ | A61B 5/415 250/362 |
| 2008/0230705 A1* | 9/2008 | Rousso | ................ | A61B 5/415 250/363.04 |
| 2009/0194677 A1* | 8/2009 | Allberg | .................. | G01T 1/20 250/252.1 |

(Continued)

FOREIGN PATENT DOCUMENTS

WO  2018052447 A1  3/2018

*Primary Examiner* — David P Porta
*Assistant Examiner* — Blake C Riddick

(57) ABSTRACT

For dose calibration in functional imaging, an amount of bias in a dose calibrator measurement of activity is determined using a spectroscopic detector. The bias may then be used to correct dose values for the same isotope used to determine a factory-based sensitivity of the functional imaging system. When local functional imaging systems are calibrated, any difference in sensitivity from the factory measured sensitivity may be due to local dose calibrator bias, so the difference in sensitivity is used to determine a local correction.

20 Claims, 3 Drawing Sheets

(56) References Cited

U.S. PATENT DOCUMENTS

| | | | | |
|---|---|---|---|---|
| 2009/0283668 A1* | 11/2009 | Gilbertson | ............. | A61B 6/037 250/252.1 |
| 2011/0147594 A1* | 6/2011 | Scoullar | ................ | A61B 6/037 250/362 |
| 2011/0178359 A1* | 7/2011 | Hirschman | ............. | G06F 19/00 600/4 |
| 2013/0124103 A1* | 5/2013 | Mabie | ..................... | G01T 1/167 702/23 |
| 2013/0131422 A1* | 5/2013 | Vosniak | ................ | A61B 6/037 600/1 |
| 2014/0151563 A1* | 6/2014 | Rousso | ................ | G01T 1/1603 250/362 |
| 2014/0163368 A1* | 6/2014 | Rousso | ................ | A61B 6/037 600/436 |
| 2014/0243500 A1* | 8/2014 | Engell | .................... | C07B 59/00 530/317 |
| 2014/0257566 A1* | 9/2014 | Engell | .................... | G16H 40/40 700/268 |
| 2014/0371580 A1 | 12/2014 | Bhattacharya | | |
| 2015/0196268 A1 | 7/2015 | Bhattacharya | | |
| 2015/0260855 A1* | 9/2015 | McQuaid | ................ | G01T 1/161 436/501 |
| 2015/0297168 A1* | 10/2015 | Panin | .................... | A61B 6/037 600/427 |
| 2017/0229202 A1* | 8/2017 | Johnson | ................ | G21G 1/001 |

\* cited by examiner

Gamma and X-ray radiation:

| | Energy (keV) | Intensity (%) | Dose (MeV/Bq-s) | |
|---|---|---|---|---|
| XR l | 3.13 | 6.78 % 17 | 2.12E-4 5 | ⎫ |
| XR kα2 | 22.984 | 24.1 % 7 | 0.00553 16 | |
| XR kα1 | 23.174 | 45.3 % 13 | 0.0105 3 | |
| XR kβ3 | 26.06 | 3.92 % 11 | 0.00102 3 | Characteristic X-rays |
| XR kβ1 | 26.095 | 7.55 % 22 | 0.00197 6 | |
| XR kβ2 | 26.644 | 1.94 % 6 | 5.18E-4 16 | ⎭ |
| | 150.81 3 | 0.0030 % 3 | 4.5E-6 5 | ⎫ |
| | 171.28 3 | 90.7 % 9 | 0.1553 16 | Gamma Emissions |
| | 245.35 4 | 94.1 % 10 | 0.2308 24 | ⎭ |

Gamma Coincidence Data  FIG. 1  (Prior Art)

ISOTOPE SPECIFIC CALIBRATION OF A DOSE CALIBRATOR FOR QUANTITATIVE FUNCTIONAL IMAGING

BACKGROUND

The present embodiments relate to calibration for functional imaging. Calibration is provided for quantitative functional imaging.

Positron emission tomography (PET) and single photon emission computed tomography (SPECT) are two types of functional or nuclear imaging. Functional imaging uses a radioisotope or radiotracer to determine metabolic function within a patient. For example, the uptake of the radiotracer by tissues in the body is measured. The emissions from the radiotracer are detected in the functional imaging. The activity concentration (i.e., the concentration of the radiotracer from different locations) is reconstructed from the detected emissions. For quantitative functional imaging, both accurate activity concentration and uptake values are desired. The goal is to provide a global baseline that is free of system (detector and dose calibrator) variability so that any measured change for a patient over time in either quantity is due to metabolic reasons.

The error in the dose applied to the patient introduces a source of error in quantitative functional imaging. A dose value is provided using a measurement by a dose calibrator. The dose value for the liquid isotope applied to the patient may be inaccurate. One source of inaccuracy is contribution from characteristic X-rays. FIG. 1 shows a table of emission spectrum for $In^{111}$. The table includes energy, the intensity (with % chance of occurring in a given instance of decay and the uncertainty), and the dose for gamma and X-ray emissions. The dose calibrator sensitivity is a highly non-linear function of incident photon or gamma energy. Primary gamma emissions from SPECT tracers are at the minimum of the chamber sensitivity while chamber sensitivity for characteristic X-ray energies of the SPECT tracers are very high. As a result, the dose calibrator measurement of activity includes a larger or comparable amount of energy from characteristic X-rays. For SPECT tracers with high energy gamma emissions in addition to the primary emissions, multiple Compton scattering of the higher energy gamma rays results in dose uncertainty.

To limit energy contribution from characteristic X-rays in dose calibration, a passive shield (e.g., copper jacket) is introduced to differentially attenuate the X-rays relative to the primary emissions. The jacket reduces but does not eliminate the X-rays, attenuates the primary emissions, and has unknown production tolerances, resulting in uncertainties of varying magnitude. For isotopes with significant emissions of characteristic X-rays, the differential attenuation of the X-rays and gamma-rays in the tracer container also creates uncertainty. For isotopes with high energy gamma emissions in addition to primary emissions, the higher efficiency for high energy gamma-rays dues to multiple Compton scattering results in calibration uncertainty.

SUMMARY

By way of introduction, the preferred embodiments described below include methods, systems, and non-transitory computer readable media for dose calibration in functional imaging. An amount of bias in a dose calibrator measurement of activity is determined using a spectroscopic detector. The bias may then be used to correct a dose value used to determine a factory-based sensitivity of the functional imaging system. When local functional imaging systems are calibrated, any difference in sensitivity from the factory measured sensitivity may be due to local dose calibrator bias, so the difference in sensitivity is used to determine a local correction.

In a first aspect, a method is provided for dose calibration for quantitative single photon emission computed tomography (SPECT). A high-purity Germanium detector measures a first activity of a radioisotope sample. The first activity is normalized by an efficiency of the high-purity Germanium detector. A dose calibrator measures a second activity of the radioisotope sample. The second activity is normalized by an efficiency of the dose calibrator. A bias is calculated based on the normalized first and second activities.

In a second aspect, a method is provided for dose calibration for quantitative nuclear imaging. A first measure of activity for a radioisotope by a spectroscopic detector is calibrated with a sensitivity of the spectroscopic detector for the radioisotope. A second measure of the activity for the radioisotope by a dose calibrator is calibrated with a sensitivity of the dose calibrator for the radioisotope. A bias is determined from the first and second measures of the activity.

In a third aspect, a system is provided for cross-calibration of dose in functional imaging quantification. A spectroscopic detector is for measuring activity of a radiotracer source. A dose calibrator is for measuring activity of the radiotracer source. A processor is configured to determine a bias of the activity measured by the dose calibrator from the activity measured by the spectroscopic detector.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a table showing the emission spectrum for $In^{111}$;

DETAILED DESCRIPTION OF THE DRAWINGS AND PRESENTLY PREFERRED EMBODIMENTS

The dose calibrator bias is eliminated for an arbitrary radioisotope, bypassing some of the intrinsic limitations of a pressurized gas ionization chamber-based dose calibrator. The bias is determined by cross-calibration with a high resolution spectroscopic detector. For example, a radioisotope in a standard geometry is calibrated using an efficiency-calibrated, high-purity Germanium (HPGe) detector. The calibration uses the primary emissions and their well-known branching ratio to normalize. The same source is calibrated in a dose calibrator. The calibration uses the sensitivity of the dose calibrator. The two calibrated measurements are used to determine the bias of the dose calibrator.

Using the spectroscopic detector for cross-calibration with the dose calibrator may more accurately correct than using an attenuation jacket. The cross-calibration is based on an absolute measurement using a high resolution spectroscopic detector. This approach is insensitive to the type of emission contamination (i.e., insensitive to low or high energy background). This approach may be applied in calibrating any isotope regardless of the complexity of the emission spectrum of the isotope.

Figure 2:
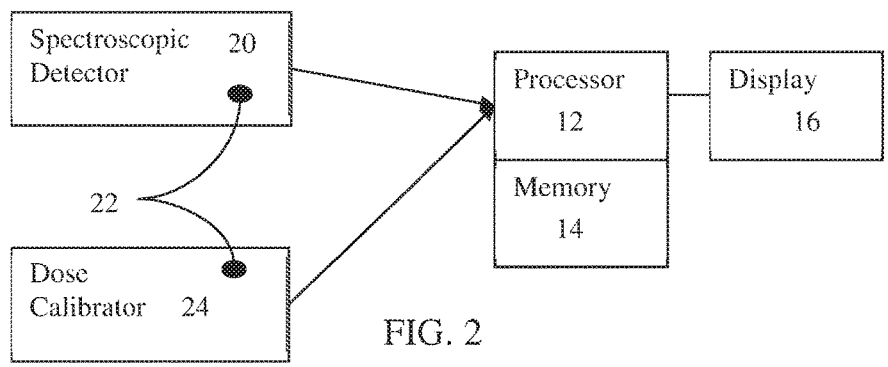
FIG. 2 is a block diagram of one embodiment of a system for cross-calibration of dose.

FIG. 2 shows one embodiment of a system for cross-calibration of dose in functional imaging quantification. The bias in a dose measurement from a dose calibrator is determined based on a spectroscopic detector. The bias may be used to correct the dose provided by dose calibrators for quantitative functional imaging.

Figure 5:
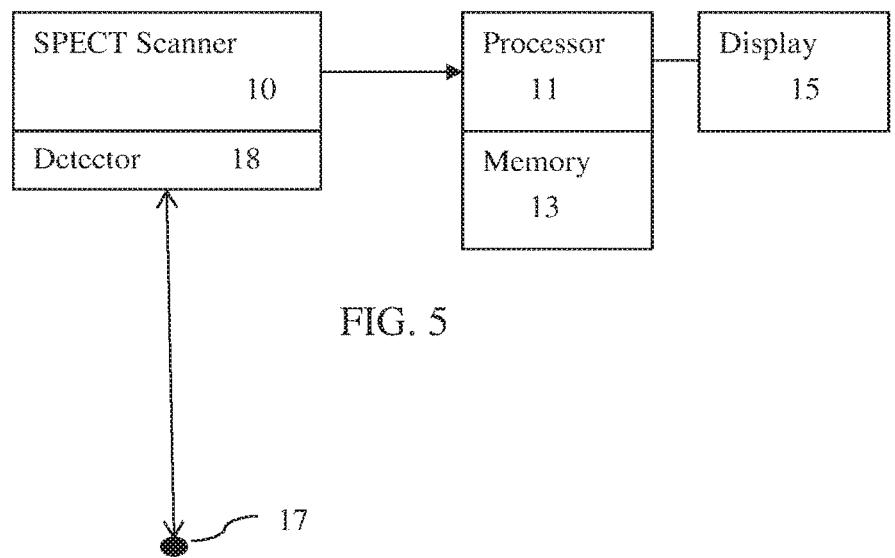
FIG. 5 is a block diagram of a SPECT system, according to one embodiment, for use of corrected dose in quantitative functional imaging.

The system of FIG. 2 is directed to determining the bias, and the system of FIG. 5 is directed to use of the bias. The system of FIG. 2 implements part of the method of FIG. 3 (e.g., acts 30-40 or 30-42). Different methods may be implemented.

The system includes a spectroscopic detector 20, a dose calibrator 24, a processor 12, a memory 14, and a display 16. Additional, different, or fewer components may be provided. For example, the memory 14 and/or display 16 are not provided. As another example, a SPECT system, PET system, other dose calibrators, and/or a user interface (input device and display 16) are provided.

In one embodiment, the system determines the biases for different radioisotopes and/or geometries. A table of biases as a function of isotope and geometry is provided to one or more functional imaging systems. A radiotracer and a dose value measured for the radiotracer by a dose calibrator of the radiotracer manufacturer are provided for functional imaging of a patient. The functional imaging system determines a dose for the provided radiotracer by applying the appropriate (e.g., by geometry and isotope) bias to the lab provided dose value. This corrected dose value may provide for more accurate activity concentration measurements and/or specific uptake value (SUV) calculations.

For determining the bias for a given isotope, a radiotracer source 22 is used. Any isotope may be included in the radiotracer, such as $In^{111}$, $I^{123}$, $I^{125}$, $Xe^{133}$, $Ce^{139}$. The radiotracer source 22 includes the pharmaceutical for binding to or attraction to functional processes in the patient tissue. Alternatively, the radiotracer source 22 includes the isotope without the pharmaceutical.

The radiotracer source 22 is packaged with any geometry. For example, the radiotracer is in a syringe. As another example, the radiotracer is encased in a metal or plastic housing of any shape. The size, shape, and/or material of the housing defines the geometry. The geometry is preferably one of commonly used geometries for radiotracers provided for functional imaging, such as a liquid radiotracer in a plastic syringe.

The spectroscopic detector 20 is a solid-state detector of gamma rays, such as having a scintillation crystal with a contact diode for sensing light generated by gamma ray interaction with the crystal. For example, the spectroscopic detector 20 is a high-purity Germanium (HPGe) detector. A cylinder of Germanium is cooled and a voltage is applied. The source 22 is positioned at one end and gamma emissions are detected with an anode and cathode arrangement in the Ge semiconductor. Other spectroscopic detectors may be used, such as based on a photo-multiplier tube.

The spectroscopic detector 20 measures activity of the radiotracer source 20. Electrical signals generated by the photon or gamma emissions interaction with the detector 20 is measured. This measure provides a dose or activity. The spectroscopic detector 20 is calibrated and capable of measuring emissions at different energies. Emissions at each energy may be separately measured, such as measuring at primary emission energies and not X-ray energies.

The dose calibrator 24 is a pressurized gas dose calibrator, such as a pressurized ion gas chamber. A pressurized gas is housed in a gap between two concentric cylinders or other shapes. The radiotracer source 22 is positioned in the inner cylinder. Emissions from the radiotracer source 22 that reach the gas may interact with the gas, creating an ion-electron pair. A voltage is applied across or between the cylinders, which act as an anode and a cathode. The energy from the ion-electron pairs is measured, providing the activity or dose of the radiotracer source 22.

The dose calibrator 24 measures activity of the radiotracer source 20. Electrical signal generated by the interaction of the emitted gamma rays with the pressurized gas is measured. This measure provides a dose or activity. The dose calibrator 24 is calibrated and measures all emissions that interact with the gas. The dose calibrator 24 is a different type of activity measuring system than the spectroscopic detector 20.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions. In one embodiment, the processor 12 is a control processor or other processor of a dose calibrator 24 or spectroscopic detector 20. In other embodiments, the processor 12 is part of a separate workstation or computer. The processor 12 is a hardware device that operates pursuant to hardware design, firmware, and/or software stored instructions to perform various acts described herein.

The processor 12 is configured to determine a bias of the activity measured by the dose calibrator 24 from the activity measured by the spectroscopic detector 20. Two measures of the activity of the same radiotracer source 22 are provided. Due to uncertainties, the measure from the dose calibrator 24 includes inaccuracies. The spectroscopic detector 20 may be less readily available, so is not used to measure dose for patient scanning. The spectroscopic detector 20 is used to determine a bias that may be applied to later measures from the dose calibrator 24 or other dose calibrators 24. The bias value is used to correct the dose measured by the dose calibrator 24 for radiotracer sources used in patient imaging. The radiotracer source 22 is used for determining the bias, but may or may not also be used for patient imaging.

The bias is a percentage difference, ratio, or other relationship between the two measures of activity. For example, the spectroscopic detector 20 measures the activity or dose as 1 millicurie, and the dose calibrator 24 measures the activity or dose of the same radiotracer source 22 as 1.5 millicurie. The bias is calculated as a percent difference (i.e., 50%), an offset (e.g., 0.5), or a ratio (e.g., 0.67 or 1.5). Other relationships between the two values may be used.

The bias is determined for a particular radioisotope and geometry of the radiotracer source 22. For example, the bias is determined for $In^{111}$ in a glass vial of a given size and shape. This bias may be used for radiotracers for patient imaging having the same radioisotope and geometry. For other isotopes and/or geometries, separate biases are determined. A table of biases as a function of isotope and geometry is created.

The value of the bias is used for sensitivity calibration. The bias is applied to dose for a source measured by a dose calibrator in a factory calibration. The bias weights the provided dose, such as by division or multiplication of the dose value by the ratio or percentage difference or adding or subtracting the offset. This bias-corrected dose is used in the factory calibration of sensitivity for the type or SPECT system. When a local SPECT system of that same type is calibrated for sensitivity, a dose from a local dose calibrator is used. If the local sensitivity (e.g., 70 CPS/Mbq or 130 CPS/Mbq) is different than the factory measured sensitivity (e.g., 100 CPS/Mbq), then the difference (e.g. 0.7 or 1.3) may be due to inaccuracy of the local dose calibrator. This difference in calibration sensitivity between the factory and local calibrations is used to correct for dose in the local SPECT system (e.g., multiply by 0.7 or 1.3). The corrected dose for any source measured by that local dose calibrator may be used by the local SPECT system in reconstruction or calculation of specific uptake values or activity concentration. The dose provided by a manufacturer of the radiotracer for a given patient is altered.

By using the sensitivity difference based on a bias correction for the factory calibration, there is no need for each clinical site to have a spectroscopic detector or having to purchase their own spectroscopic detector (e.g., HPGe) calibrated liquid sources to eliminate the biases in their local dose calibrators. In alternative embodiments, the bias correction is performed locally to a given SPECT system. The bias is calculated and used to correct the dose of the local calibrator for a radiotracer to be used for a given patient.

The bias, measured dose from the spectroscopic detector 20, measured dose from the dose calibrator 24, and/or factory calibrated sensitivity may be stored in the memory 14. A corrected dose value may be stored in the memory 14. Any of the bias, measurements, or dose values may be displayed on the display 16.

Figure 3:
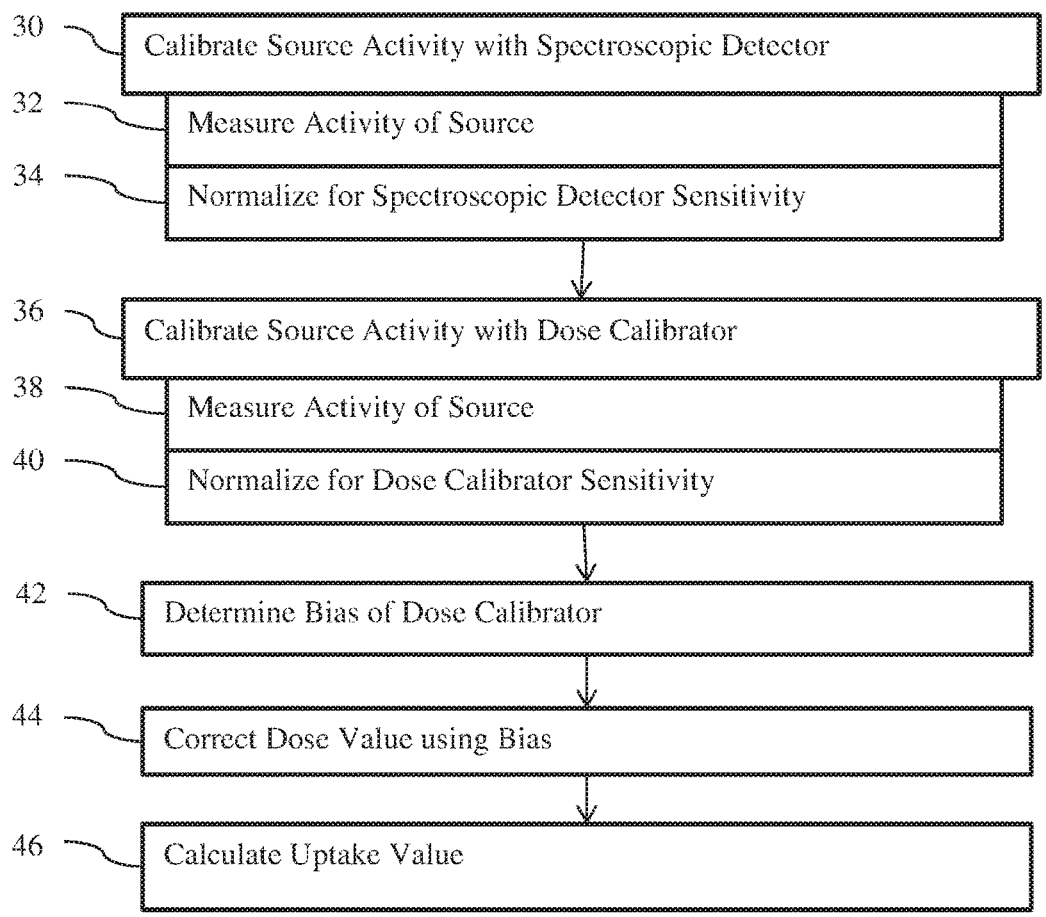
FIG. 3 is a flow chart diagram of one embodiment of a method for dose calibration for quantitative nuclear imaging.

FIG. 3 shows one embodiment of a method for dose calibration for quantitative nuclear imaging (e.g., single photon emission computed tomography (SPECT) or positron emission tomography (PET) quantitative imaging). The examples below are provided for SPECT, but may be used in PET or other functional imaging modality. Other functional imaging may be used. The dose is calibrated in a way removing variability by applying a correction factor based on comparative measures of activity between a dose calibrator and a spectroscopic detector. For activity concentration estimation or uptake calculation (e.g., specific uptake value calculation), a factory calibrated sensitivity based on the bias corrected dose is compared to a local calibrated sensitivity. Any difference is used to correct dose from the local dose calibrator in estimation of concentration or uptake calculation. The method of FIG. 3 is directed to the determination of the bias, the use of the bias for factory calibration of sensitivity, and use of the factory calibration of sensitivity for does correction at a local system.

For use, the method is applied for a given scan of a given patient. By applying the method to different scans of the patient, the resulting quantities may be compared and have little to no variance due to differences in dose. The different scans use the same or different detectors and/or doses. Similarly, the SUV quantities may be compared between patients to establish norms or deviation from norm. Without the dose calibration, comparison of activity concentration or uptake over time is subject to variance unrelated to the metabolic function of the patient or patients.

The radioisotope sample used for determining the bias (i.e., used in acts 30 and 36) is a different sample than is used in acts 44 and 46. The sample may be different, but the geometry and/or isotope is the same.

Additional, different, or fewer acts may be performed. For example, acts 44 and 46 are not provided. As another example, acts 30-42 are not provided. In other examples, acts related to positioning, configuring, and/or activating are provided.

The acts are performed in the order shown or a different order. For example, act 36 is performed prior to act 30.

In act 30, a measure of activity for a radioisotope is calibrated by a spectroscopic detector. Acts 32 and 34 are an example of this calibration. The spectroscopic detector measures the activity in act 32, and a processor normalizes the measured activity to account for a sensitivity of the spectroscopic detector for the radioisotope in act 34. Other acts may be provided.

In act 32, a high-purity Germanium (HPGe), efficiency calibrated HPGe, or other spectroscopic detector measures an activity of a radioisotope sample. The activity is measured for one or more primary emission energies. For example, the activity for a radioisotope sample of In111 is measured at 171 and 245 keV and not at other energies (see FIG. 1). The energies in a range may be measured, such as with tolerance about one or more primary gamma emission energies for the isotope. X-ray energies are not measured. The measure may be activity for one energy window or may be activity in a combination of energies.

The measurement is of a radioisotope sample in a given container with a given geometry. The measures of act 32 and 38 are of the same sample, so are measures with the same sample geometry and radioisotope. The calibration is geometry and radioisotope specific.

In act 34, the measured activity from the spectroscopic detector is normalized. The spectroscopic detector has a calibrated efficiency or sensitivity to the radioisotope and/or at the energies being measured. The efficiency accounts for the branching ratio of the isotope. The efficiency accounts for emissions at other energies, indicating an adjustment to the measurements at the primary energies to more likely provide the actual dose of the radioisotope sample.

The measurement is weighted by the efficiency or sensitivity. For example, the measured activity is multiplied by the known efficiency of the spectroscopic detector to provide a more accurate dose. Where the primary energies are measured separately, the same or energy-specific efficiencies are used.

In act 36, a measure of activity for a radioisotope is calibrated by a dose calibrator. Acts 38 and 40 are an example of this calibration. The dose calibrator measures the activity in act 38, and a processor normalizes the measured activity to account for a sensitivity of the dose calibrator for the radioisotope in act 40. Other acts may be provided.

In act 38, the dose calibrator, such as a pressurized-gas ion chamber, measures an activity of the radioisotope sample. The same sample with the same geometry and/or isotope is measured in act 38 as is measured in act 32. The measurement is of the radioisotope sample in the given container with the given geometry. The calibration is geometry and radioisotope specific.

The activity is measured for the total energy deposited by the emissions per unit time. The activity measured includes energy from the primary emissions as well as energy from other gamma and/or X-ray emissions. For example, the activity for a radioisotope sample of $In^{111}$ is measured across all the energies of the radiation (see FIG. 1).

Figure 4:
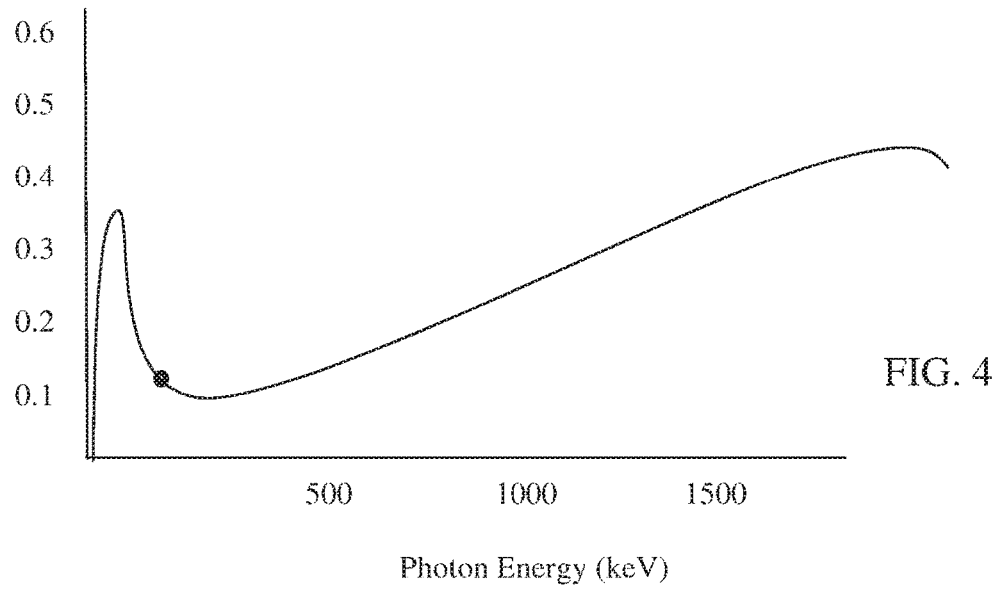
FIG. 4 is an example graph of dose calibrator sensitivity.

In act 40, the measured activity from the dose calibrator is normalized. The dose calibrator has a calibrated efficiency or sensitivity to the radioisotope. The efficiency accounts for chamber sensitivity and the amount of energy from the primary gamma emissions relative to the other emissions of the isotope. FIG. 4 shows an example for $In^{111}$ (dot on the sensitivity curve). $In^{111}$ emits primary energies at 171 and 245 keV, so the sensitivity of the dose calibrator is about 0.13. The sensitivity for X-ray energies around 20-30 keV may be 0.3. The efficiency indicates an adjustment to the measurements to account for the difference in sensitivity in detecting emissions at X-ray energies, secondary gamma energies, and primary gamma energies. The normalization corrects the measured activity to more likely provide the actual dose of the radioisotope sample at the primary emission energy or energies.

The measurement is weighted by the efficiency or sensitivity. For example, the measured activity is multiplied by the known efficiency of the dose calibrator to provide a more accurate dose. The measured energy is normalized by chamber sensitivity and primary emission branches to compute decays per second (Bq).

In act 42, a processor determines a bias from the measures of the activity. The normalized measures are cross-calibrated. For example, a ratio, percentage difference, offset, or other relationship between the measures from the dose calibrator and the spectroscopic detector is calculated.

The bias is calculated for the radioisotope sample. The bias is specific to the geometry and/or isotope in the sample. The calibrations and determination of bias may be repeated for different geometry and isotope combinations. The bias indicates an amount of inaccuracy in the dose from the dose calibrator, so is used to correct. The absolute measurement from the spectroscopic detector is used to correct the dose from less accurate dose calibrators. Due to the spectroscopic detector's ability to measure as specific energies, the bias may be applied for isotopes with any emission spectrum.

In act 44, a processor corrects the dose value of a radiotracer using the bias. The bias is determined using acts 30-42. This bias is then stored and/or used for factory calibration of sensitivity.

The lab providing the liquid radiotracer to inject into the patient provides dose, such as a value in Becquerel. This dose is of the same isotope and same type of liquid radiotracer used for the factory calibration measurements, but may be of a different type of radiotracer. The lab provides the dose value of the liquid radiotracer measured using a local dose calibrator. This provided local dose from the local dose calibrator is used to calibrate the sensitivity of the local functional imaging system. The factory calibrated sensitivity based on the bias corrected dose is compared to the local calibrated sensitivity based on the dose from the local dose calibrator. If the sensitivities differ by a threshold amount or any amount, then a ratio or other difference is determined. This difference is a correction factor to be applied to any dose for the isotope and geometry from the local dose calibrator. This corrected dose for any dose applied to a patient may remove inconsistency due to local dose calibrator variation. In alternative embodiments, the correction based on the difference in sensitivities is applied to the local sensitivity.

The local corrected dose value is used in calculating uptake from the activity concentration. Prior to such use, the dose value is corrected using the difference in factory and local calibration sensitivities. The correction is a multiplication, division, addition, or subtraction. Other functions may be used. In alternative embodiments, the local correction factor is used to look-up a weight or other adjustment applied to the dose value. In either the direct or indirect sense, the injected dose value for a radiotracer used in a patient is corrected. The correction indicates an amount of error in the dose calibrator measurements, so weights the local dose value. The correction provides a more accurate dose from a dose calibrator due to use of the high resolution spectroscopic measurement to determine the bias in the factory calibration of sensitivity. This approach may be insensitive to the type of emission contamination (e.g., low or high energy background). The correction may be applied in calibrating any isotope regardless of the complexity of the emission spectrum. Correcting the injected dose by may result in more accurate uptake values free of or with reduced local dose calibrator-specific variations.

In act 46, a functional imaging system (e.g., SPECT system) estimates the activity concentration. The activity concentration in a patient having received the liquid radiotracer is determined as part of reconstruction. After ingesting or injecting the radiotracer into the patient, the patient is positioned relative to the detector and/or the detector is positioned relative to the patient. Emissions from the radiotracer within the patient are detected over time.

To determine the locations within the patient at which the emissions occurred, the detected emissions are reconstructed into an object space. Distribution of emissions in a volume or image data is reconstructed. The quantity or amount of uptake for each location (e.g., voxel) is estimated. The SPECT imaging system estimates the activity concentration of an injected radio-pharmaceutical or tracer for the different locations. In quantitative SPECT, the goal is to estimate the activity concentration in kBq/ml of the tracer (i.e., isotope) that was injected into and distributed within the patient.

For reconstruction, the activity concentration (e.g., quantitative SPECT) is reconstructed using a system matrix. The reconstruction is iterative and contains a model of the imaging formation physics as a pre-requisite of quantitative reconstruction. The image formation model includes the detected data (e.g., counts), the system matrix, isotope properties (e.g., corrected dose value), and biology. The system matrix represents mechanical properties of the system, but may include other information (e.g., injection time and patient weight as represented by SUV).

Reconstruction includes a projection operator to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The reconstruction uses the system matrix representing various aspects of the detection of the emissions, including modeling the imaging physics. The imaging physics includes aspects of the SPECT system, such as calibration of the SPECT system. The system matrix includes the detector sensitivity, such as the system specific sensitivity to the liquid radiotracer used in the patient. The corrected dose is included as part of the system matrix or as a separate isotope data used in reconstruction. Alternatively or additionally, a corrected sensitivity to account for local dose calibrator variance is used.

Specific uptake values (SUVs) are calculated by the processor of the functional imaging system. The activity concentration represents the amount of uptake at each location. This amount of uptake is a measure of emitted radiation, so is not normalized for the radiation dose provided to the patient. As a result, comparing uptake from different times may not be useful unless the same dose is provided. By calculating the SUV, uptake normalized for dose is provided, allowing comparison of different measures.

The SUV for each location or for some of the locations is calculated. The SUV is a function of the activity concentration for that location and the corrected dose value from act 44. The activity concentration is divided by the corrected injected dose value. Other functions may be used. For example, the SUV may be a function of the body mass or other physical characteristic of the patient. The uptake magnitude represented in the activity concentration is normalized for both dose and body mass.

Due to the cross-calibration for the dose using the local and factory calibrated sensitivities, the SUV may be more accurately compared over time or from different examinations. Different radiotracer dose and/or different detectors may be used. Where the different examinations use the correction for bias based on the spectroscopic detector, the resulting difference in SUVs more likely represents diagnostic or metabolic difference rather than difference due to variance in detector or dose. Quantification in functional imaging, such as SPECT, provides both accurate activity concentration and accurate SUVs.

Further calibration and/or use of the corrected dose may be provided. For example, the spectroscopic detector-based bias of dose from dose calibrators taught herein is used for functional imaging as discussed in U.S. Published Patent Application Nos. 2014/0371580 or 2015/0196268, or PCT Application No. PCT/US2016/052457, filed Sep. 19, 2016. Any dose or dose correction in those teachings may be corrected for the cross-calibration using the spectroscopic detector discussed herein.

FIG. 5 shows a system for functional imaging using corrected dose values. The system includes an SPECT scanner 10, a processor 11, a memory 13, and a display 15. The processor 11, memory 13, and/or display 15 are part of the SPECT scanner 10 or are separate (e.g., a computer or workstation). The processor 11, memory 13, and/or display 15 may be the processor 12, memory 14, and/or display 16, respectively of FIG. 2 or are separate devices. Additional, different, or fewer components may be provided. For example, the system is a computer without the SPECT scanner 10. As another example, user input, patient bed, or other SPECT related devices are provided. Other parts of the system may include power supplies, communications systems, and user interface systems. In yet another example, a PET scanner or other functional imaging system is provided instead of the SPECT scanner 10.

The SPECT scanner 10 is a SPECT system. As a SPECT system, a detector 18 is provided. Other components may be provided, such as collimator. Any now known or later developed SPECT scanner 10 may be used.

The detector 18 is a gamma camera connected with a gantry. The gamma camera is a planar photon detector, such as having crystals or scintillators with an optical detector. The gantry rotates the gamma camera about the patient. During scanning of a patient, emission events are detected with the camera at different positions or angles relative to the patient. The emission events are from a radiotracer 17 in the patient.

The SPECT scanner 10, using the detector 18, detects emissions from the radiotracer 17. The radiotracer 17 shares a radioisotope and geometry with the sample 22, but may be a different sample from a different or same lab. For imaging uptake in a patient, the detector 18 detects emissions from the patient. The emissions occur from any location in a finite source (i.e., the patient). The radiotracer 17 in the patient migrates to, connects with, or otherwise concentrates at specific types of tissue or locations associated with specific biochemical reactions. As a result, a greater number of emissions occur from locations of that type of tissue or reaction. For example, the radiotracer 17 is designed to link with locations of glucose uptake, fatty acid synthesis, or other metabolic process.

The SPECT scanner 10 is configured to reconstruct the imaged volume by applying a system matrix to the detected data. The processor 11 is used to perform the reconstruction, or the SPECT scanner 10 has another processor that performs the reconstruction. Any reconstruction may be used to estimate the activity concentration in the patient. The SPECT scanner 10 accesses the detected emission events from the memory 13 or buffers to reconstruct. The system matrix includes a system sensitivity for the liquid radiotracer provided to the patient. This sensitivity is used for the reconstruction. Differences between the local calibrated sensitivity and a factory calibrated sensitivity based on the bias corrected dose are used to correct for local dose calibration measurements. The reconstruction also uses a sensitivity-based correction of dose value for the radiotracer applied to the patient. The corrected dose is used.

The processor 11 is configured by software, firmware, and/or hardware. The processor 11 operates pursuant to stored instructions to perform various acts described herein, such as correcting of act 44 and the calculation of SUV of act 46. The processor 11 receives, looks-up, or accesses a bias or a factory-calibrated sensitivity for a given isotope and geometry corresponding to the isotope and geometry of the radiotracer 17 to be used in the patient. For factory sensitivity calibration, the processor 11 uses the bias to correct the dose from the dose calibrator. For a patient scan, the processor 11 uses the factory-calibrated sensitivity based on the bias correction to determine a local correction for the dose. The factory-calibrated sensitivity is based on the bias determined for a factory dose calibrator. The processor 11 corrects a dose value for the radiotracer 17 using a correction based on a difference between the factory calibrated sensitivity and the locally measured sensitivity. The processor 11 is configured to correct the input dose of the liquid radiotracer provided to the patient. For example, the ratio of sensitivities is multiplied with the dose. Based on this corrected dose, the processor 11 is configured to reconstruct activity concentration and/or calculate SUVs. The SUV at one or more locations are calculated by normalizing the activity concentration with the corrected dose. The resulting SUVs have less variability due to the system and/or dose, so more likely represent changes in metabolic function of the patient.

The bias, dose value, scan data, sensitivities, corrected dose, measured activity, efficiencies, and/or other information are stored in the memory 13 and/or 14. The data is stored in any format. The memories 13, 14 are a buffer, cache, RAM, removable media, hard drive, magnetic, optical, database, or other now known or later developed memory. Each of the memories 13, 14 is a single device or group of two or more devices. In one embodiment, the memory 13 stores a table of biases, sensitivities, and/or corrections based on differences in sensitivities as a function of isotope and geometry. The table is transferred to the memory 14 of a functional imaging system for use in correcting dose from a dose calibrator of a laboratory local to the SPECT scanner 10.

The memories 13, 14 are additionally or alternatively a non-transitory computer readable storage medium with processing instructions. The memories 13, 14 store data representing instructions executable by the programmed processors 11, 12, respectively. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The displays 15, 16 are a CRT, LCD, plasma screen, projector, printer, or other output device for showing an image. The display 16 displays a bias, dose, sensitivity, measured activity, and/or corrected dose. The display 15 displays an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. The corrected dose may be displayed as an annotation with the image. Alternatively or additionally, any quantities derived by the processor 11 may be displayed, such as corrected dose, dose and bias, sensitivity, SUVs, and/or change in SUV. Other quantities may be determined, such as average SUV or activity concentration for a region, maximum SUV, peak SUV in a predetermined unit volume, variance in activity concentration, or total SUV.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for dose calibration for quantitative single photon emission computed tomography (SPECT), the method comprising:
    measuring a first activity of a radioisotope sample with a high-purity Germanium detector, the radioisotope sample having a radioisotope;
    normalizing the first activity by an efficiency of the high-purity Germanium detector;
    measuring a second activity of the radioisotope sample with a first dose calibrator of a first SPECT system;
    normalizing the second activity by an efficiency of the first dose calibrator;
    calculating a bias based on the normalized first and second activities;
    correcting a dose value of a radiotracer of the radioisotope with a difference in sensitivity based on the bias;
    determining the difference in sensitivity by applying the calculated bias to a table of dose values for the radiotracer, the table having values measured by a second dose calibrator remote from the first SPECT system unit.

2. The method of claim 1 wherein measuring the first activity comprises measuring with the high-purity Germanium detector comprising an efficiency calibrated high-purity Germanium detector.

3. The method of claim 1 wherein measuring the first activity comprises measuring the first activity at one or more primary emission energies, and wherein measuring the second activity comprises measuring the second activity at a range of energies including the primary emission energies and x-ray energies.

4. The method of claim 1 wherein measuring the first activity comprises measuring the first activity with the radioisotope sample being in a container having a geometry, wherein measuring the second activity comprises measuring the second activity with the radioisotope sample being in the container with the geometry, and wherein calculating the bias comprises calculating the bias specific to the geometry and the radioisotope.

5. The method of claim 1 wherein normalizing the first and second activities comprise weighting the respective efficiencies, the efficiencies comprising sensitivities of the high-purity Germanium detector and the dose calibrator.

6. The method of claim 1 wherein normalizing the first and second activities comprise weighting by the respective efficiencies for a radioisotope for the radioisotope sample.

7. The method of claim 1 wherein measuring the second activity comprises measuring with the dose calibrator comprising a pressurized-gas ion chamber dose calibrator.

8. The method of claim 1 wherein normalizing the first activity comprises normalizing with the efficiency accounting for a branching ratio of a radioisotope of the radioisotope sample.

9. The method of claim 1 wherein calculating the bias comprises calculating a ratio of the normalized first and second activities.

10. The method of claim 1, further comprising:
    estimating, by a SPECT system, specific uptake values in a patient having the radiotracer with the corrected dose value.

11. The method of claim 10 wherein estimating comprises reconstructing the activity concentration from counts measured with a gamma camera of the SPECT system from the radiotracer in the patient, the reconstructing being a function of a system matrix for the SPECT system and calculating the specific uptake values as a function of the activity concentration and the corrected dose value.

12. A method for dose calibration for quantitative nuclear imaging, the method comprising:
    measuring a first measure of activity for a radioisotope;
    measuring a second measure of activity for the radioisotope;

calibrating the first measure by a spectroscopic detector with a sensitivity of the spectroscopic detector for the radioisotope;

calibrating the second measure of the activity for the radioisotope by a first dose calibrator of a first SPECT system with a sensitivity of the dose calibrator for the radioisotope;

determining a bias from the first and second measures of the activity;

correcting a dose value of a radiotracer of the radioisotope with a difference in sensitivity based on the bias; and determining the difference in sensitivity by applying the determined bias to a table of dose values for the radiotracer, the table having values measured by a second dose calibrator remote from the first SPECT system unit.

13. The method of claim 12 wherein the calibrating of the first and second measures comprises calibrating with the first and second measures being of a same sample of the radioisotope.

14. The method of claim 13 wherein calibrating for the same sample comprises calibrating for a geometry of the sample, and wherein determining the bias comprises determining the bias specific to the geometry and the radioisotope.

15. The method of claim 12 wherein determining the bias comprises calculating a percentage difference between the first and second measures.

16. The method of claim 12 wherein determining the bias comprises cross-calibrating the first and second measures.

17. A system for cross-calibration of dose in functional imaging quantification, the system comprising:
a radiotracer source;
a spectroscopic detector for measuring a first activity of the radiotracer source;
a first dose calibrator for measuring a second activity of the radiotracer source;
a memory containing executable instructions;
a processor configured to execute the executable instructions, the executable instructions causing the processor to:
determine a bias of the second activity measured by the first dose calibrator from the first activity measured by the spectroscopic detector;
cross-calibrate the dose with a difference in sensitivity based on the bias; and
determining the difference in sensitivity by applying the determined bias to a table of dose values for the radiotracer, the table having values measured by a second dose calibrator of a second system remote from the first dose calibrator.

18. The system of claim 17 wherein the spectroscopic detector comprises a high-purity Germanium detector.

19. The system of claim 17 wherein the dose calibrator comprises a pressurized gas dose calibrator.

20. The system of claim 17 wherein the processor is configured to determine the bias as a function of a geometry of the radiotracer source and a radioisotope of the radiotracer source.

* * * * *